United States Patent [19]

Oekonomopulos et al.

[11] Patent Number: 5,025,010
[45] Date of Patent: Jun. 18, 1991

[54] BENZOTHIAZINONE DERIVATIVES, AND PHARMACEUTICALS CONTAINING THEM

[75] Inventors: Raymond Oekonomopulos, Wiesbaden; Rainer Henning, Hattersheim am Main; Ulrich Lerch, Hofheim am Taunus; Bernward Schölkens; Wolfgang Linz, both of Kelkheim, all of Fed. Rep. of Germany

[73] Assignee: Hoechst Aktiengesellschaft, Frankfurt am Main, Fed. Rep. of Germany

[21] Appl. No.: 423,714

[22] Filed: Oct. 17, 1989

Related U.S. Application Data

[63] Continuation of Ser. No. 222,607, Jul. 21, 1988, abandoned.

[30] Foreign Application Priority Data

Jul. 23, 1987 [DE] Fed. Rep. of Germany ....... 3724366

[51] Int. Cl.⁵ .................... C07D 279/16; A61K 31/54
[52] U.S. Cl. ..................................... 514/224.2; 544/52
[58] Field of Search ........................ 544/52; 514/224.2

[56] References Cited

U.S. PATENT DOCUMENTS

| | | | |
|---|---|---|---|
| 4,584,300 | 4/1986 | Iwao et al. ........................... | 514/225 |
| 4,595,685 | 6/1986 | Henning et al. ..................... | 514/225 |
| 4,831,028 | 5/1989 | Lerch et al. ....................... | 514/224.2 |

FOREIGN PATENT DOCUMENTS

| | | |
|---|---|---|
| 116368 | 7/1984 | European Pat. Off. . |
| 146893 | 7/1985 | European Pat. Off. . |
| 3514355 | 10/1987 | European Pat. Off. . |
| 3614363 | 10/1987 | European Pat. Off. . |
| 86/05490 | 9/1986 | World Int. Prop. O. . |

OTHER PUBLICATIONS

Cram and Allinger, J. Am. Chem. Soc., 78, (1956), pp. 2518–2524.
Iwao et al., CA 104:109666p (1986), Chemical Abstracts.

*Primary Examiner*—John M. Ford
*Attorney, Agent, or Firm*—Finnegan, Henderson, Farabow, Garrett, and Dunner

[57] ABSTRACT

A description is given of compounds I

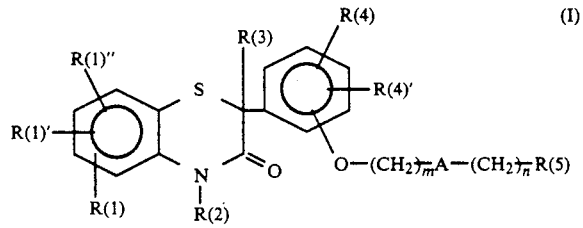

with R(1) equal to H, alkyl, alkoxy, Hal, $NO_2$, OH, acetamido or amino; R(2) equal to H, alk(en)yl or phenylalkyl; R(3) equal to H, (cyclo)alk(en)yl(alkyl), phenyl or phenylalkyl; R(4) equal to H, alkyl, alkoxy, Hal $CF_3$, $NO_2$, OH, acetamido or amino; A equal to —C≡C— or —CH=CH—; R(5) equal to various amines; m and n equal to 1–3; and their salts. Preparation processes are also described. Compounds I are excellent calcium agonists or calcium antagonists. They also act to regulate the blood glucose.

8 Claims, No Drawings

BENZOTHIAZINONE DERIVATIVES, AND PHARMACEUTICALS CONTAINING THEM

This application is a continuation of application Ser. No. 07/222,607 filed Jul. 21, 1988 now abandoned.

It is known that compounds which prevent the influx of calcium ions into cells can be used as therapeutics for the treatment of various diseases, in particular of the cardiovascular system in humans and other warm-blooded species.

Benzothiazinone derivatives acting as calcium antagonists are described in EP-A-116,368; the compounds listed therein are unsubstituted in the 2-position of the heterocycle.

Benzothiazinone derivatives acting as calcium antagonists are also to be found in EP-A-146,893. The compounds described therein have a basic ether grouping on the 2-phenyl radical, the basic nitrogen being bonded via a straight-chain or branched alkyl chain to the ether oxygen.

We have now found, surprisingly, that compounds having a modified side chain have properties in which either calcium antagonism or calcium agonism predominates depending on the nature of the side chain. The latter property makes the relevant compounds suitable, inter alia, for the treatment of cardiac insufficiency and of hypotension.

Hence the invention relates to benzothiazinone derivatives of the formula I which act as calcium antagonists or calcium agonists.

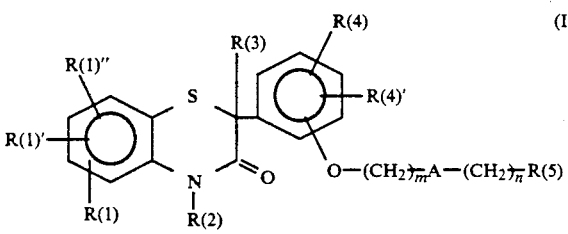

in which formula I;

R(1), R(1)' and R(1)" are identical or different and denote, independently of one another, hydrogen, $(C_1-C_4)$-alkyl, $(C_1-C_3)$-alkoxy, F, Cl, Br, $CF_3$, nitro, hydroxyl, acetamido or amino, R(2) denotes hydrogen, $(C_1-C_{10})$-alkyl, straight-chain or branched, $(C_3-C_{10}$-alkenyl, straight-chain or branched, phenyl-$(C_1-C_4)$-alkyl, the phenyl ring being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(3) denotes hydrogen, $(C_1-C_{15})$-alkyl, straight-chain or branched, $(C_3-C_{15})$-alkenyl, straight-chain or branched, $(C_4-C_8)$-cycloalkyl, $(C_4-C_8)$-cycloalkyl-$(C_1-C_4)$-alkyl, phenyl or phenyl-$(C_1-C_4)$-alkyl, each of the phenyl radical being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(4) and R(4)' are identical or different and denote, independently of one another, hydrogen, $(C_1-C_4)$-alkyl, $(C_1-C_3)$-alkoxy, F, Cl, $CF_3$, nitro, hydroxyl, acetamido or amino, A denotes a group $-C\equiv C-$ or a group $-CH=CH-$ which has the cis or trans configuration, R(5) denotes one of the following groups

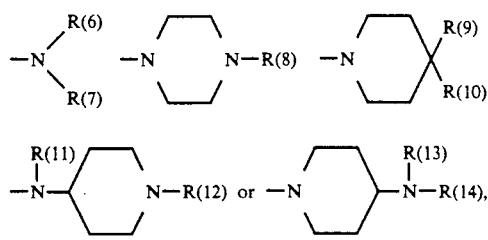

in which

R(6) and R(7) are identical or different and denote, independently of one another, hydrogen, $(C_1-C_{10})$alkyl, $C_4-C_8$)-cycloalkyl, $C_4-C_8$)-cycloalkyl-$(C_1-C_4)$-alkyl, pyridyl-$(C_1-C_4)$-alkyl, phenyl-$(C_1-C_6)$-alkyl, benzhydryl or benzhydryl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(8) denotes hydrogen, $(C_1-C_{10})$-alkyl, straight-chain or branched, $C_1-C_8$)-alkanoyl, pyridyl, pyrimidinyl, phenyl, phenyl-$(C_1-C_4)$-alkyl, phenyl-$(C_3-C_5)$-alkenyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(9) denotes hydrogen, $(C_1-C_{10})$-alkyl, phenyl, phenyl($C(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(10) denotes hydrogen, hydroxyl or $(C_1-C_4)$-alkoxy, and R(11) and R(12) or R(13) and R(14) are identical or different and denote, independently of one another, hydrogen, $(C_1-C_{10})$-alkyl, straight-chain or branched, $(C_1-C_6)$-alkanoyl, phenyl-$(C_1-C_4)$-alkyl, benzhydryl, or benzhydryl-$(C_1-C_4)$-alkyl, phenyl-$(C_1-C_4)$-alkanoyl or benzoyl, each of the phenyl radical being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, m denotes 1, 2 or 3, and n denotes 1, 2 or 3, and the salts of the compounds of the formula I with pharmaceutically acceptable acids.

Preferred compounds of the formula I are those in which at least one of the substituents or indices has the following meaning:

R(1) and R(1)', identical or different and independently of one another, hydrogen, methyl, ethyl, methoxy, ethoxy, fluorine, chlorine, $C_3$, nitro or acetamido, R(1)" hydrogen, R(2) hydrogen, $(C_1-C_6)$-alkyl, straight-chain or branched, allyl, methallyl, benzyl, phenethyl, 4-methoxybenzyl, 3,4-dimethoxybenzyl, 3,4,5-trimethoxybenzyl, 3,4-methylenedioxybenzyl, R(3) hydrogen, $(C_1-C_{12})$-alkyl, straight-chain or branched, allyl, methallyl, $(C_5-C_7)$-cycloalkyl, $(C_5-C_7)$-cycloalkyl-$(C_1-C_4)$-alkyl, benzyl, methylbenzyl, fluorobenzyl, methoxybenzyl, dimethoxybenzyl or phenylethyl, R(4) hydrogen, methyl, methoxy, ethoxy, chlorine, nitro, hydroxyl, acetamido or amino, R(4)' hydrogen, A a group —C≡C— or a group —C=CH— which has the cis or trans configuration, R(5) one of the following groups

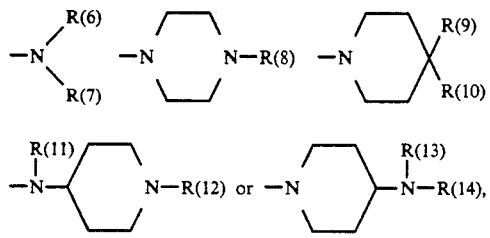

in which

R(6) denotes hydrogen, methyl, ethyl, propyl or isopropyl,

R(7) denotes hydrogen, methyl, ethyl, propyl, isopropyl, cyclopentylethyl, cyclohexylethyl, phenyl-($C_1$-$C_4$)-alkyl, benzhydryl or benzhydryl-($C_1$-$C_4$)-alkyl, each of the phenyl radicals being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, $CF_3$ or hydroxyl, or denotes pyridyl-($C_1$-$C_4$)-alkyl, R(8) denotes hydrogen, ($C_1$-$C_6$)-alkyl, straight-chain or branched, ($C_1$-$C_6$)-alkanoyl, phenyl, the phenyl radical being unsubstituted or substituted by one or two radicals from the group comprising ($C_1$-$C_4$)-alkyl, ($C_1$-$C_4$)-alkoxy, ($C_1$-$C_2$)-alkylenedioxy, F, Cl, $CF_3$ or hydroxyl, or denotes phenyl-($C_1$-$C_4$)-alkyl, phenyl-($C_3$-$C_5$)-alkenyl, benzhydryl or benzhydryl-($C_1$-$C_4$)-alkyl, phenyl-($C_1$-$C_4$)-alkanoyl or benzoyl, each of the phenyl radicals being unsubstituted or substituted by one, two or three radicals from the group comprising methyl, ethyl, methoxy, ethoxy, ($C_1$-$C_2$)-alkylenedioxy, F, Cl, $CF_3$ or hydroxyl, R(9) denotes phenyl, phenyl-($C_1$-$C_4$)-alkyl, each of the phenyl radicals being unsubstituted or substituted by one, two or three radicals from the group comprising ($C_1$-$C_4$)-alkyl, ($C_1$-$C_4$)-alkoxy, ($C_1$-$C_2$)-alkylenedioxy, F, Cl, $CF_3$ or hydroxyl, R(10) denotes hydrogen, hydroxyl or methoxy, R(11), R(12), R(13) and R(14) are identical or different and denote hydrogen, $C_1$-$C_8$-alkyl, ($C_1$-$C_6$)-alkanoyl, phenyl-($C_1$-$C_4$)-alkyl, benzhydryl or benzhydryl-($C_1$-$C_4$)-alkyl, phenyl-($C_1$-$C_4$)-alkanoyl or benzoyl, each of the phenyl radicals being unsubstituted or substituted by one, two or three radicals from the group comprising methyl, ethyl, methoxy, ethoxy, ($C_1$-$C_2$)-alkylenedioxy, F, Cl, $CF_3$ or hydroxyl, m denotes 1 or 2, and n denotes 1 or 2 and the salts of these compounds of the formula I with pharmaceutically acceptable acids.

Particularly preferred compounds of the formula I are those in which at least one of the substituents or of the indices has the following meaning:

R(1) hydrogen, methyl, methoxy, fluorine or chlorine,

R(1)' hydrogen or methoxy,

R(1)" hydrogen,

R(2) hydrogen, methyl, ethyl, propyl, isopropyl, butyl, sec. butyl, isobutyl, benzyl or phenethyl, R(3) hydrogen, ($C_1$-$C_{12}$)-alkyl, straight-chain or branched, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) hydrogen, methoxy, methyl, chlorine, nitro or hydroxyl, R(4)' hydrogen, A a group —C≡C—, or a group —CH=CH— which has the cis or trans configuration, R(5) one of the following groups

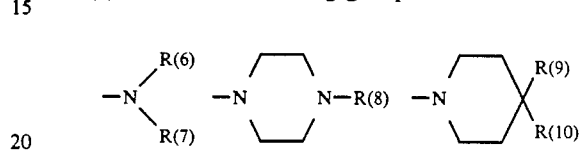

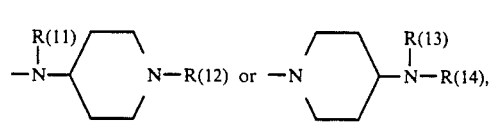

in which

R(6) denotes hydrogen or methyl,

R(7) denotes phenyl-($C_1$-$C_4$)-alkyl, benzhydryl or benzhydryl-($C_1$-$C_4$)-alkyl, each phenyl radical being unsubstituted or substituted by one, two or three radicals from the group comprising methyl, methoxy, fluorine, chlorine, methylenedioxy or hydroxyl, R(8) denotes ($C_1$-$C_6$)-alkyl, straight-chain or branched, ($C_1$-$C_6$)-alkanoyl, phenyl, phenyl-($C_1$-$C_4$)-alkyl, benzhydryl or benzhydryl-($C_1$-$C_4$)-alkyl, phenyl-($C_1$-$C_4$)-alkanoyl or benzoyl, each of the phenyl radicals being unsubstituted or substituted by one, two or three radicals from the group comprising methyl, methoxy, ethoxy, methylenedioxy, fluorine, chlorine or hydroxyl, R(9) denotes phenyl, the phenyl radical being unsubstituted or substituted by one, two or three radicals from the group comprising methyl, methoxy, fluorine, chlorine, methylenedioxy or hydroxyl, R(10) denotes hydrogen, hydroxyl or methoxy, R(11), R(12), R(13) and R(14) are identical or different and denote hydrogen, ($C_1$-$C_6$)-alkyl, ($C_1$-$C_6$)-alkanoyl, phenyl-($C_1$-$C_4$)-alkyl, benzhydryl or be hydryl-($C_1$-$C_4$)-alkyl, phenyl-($C_1$-$C_4$)-alkanoyl or benzoyl, each of the phenyl radicals being unsubstituted or substituted by one, two or three radicals from the group comprising methyl, methoxy, methylenedioxy, fluorine, chlorine or hydroxyl, m and n 1, and the salts of these compounds of the formula I with pharmaceutically acceptable acids.

The pharmaceutically acceptable acids which are suitable are inorganic acids such as hydrochloric acid, hydrobromic acid, hydriodic acid, sulfuric acid, phosphoric acid or nitric acid, or organic acids such as tartaric acid, malic acid, lactic acid, maleic acid, fumaric acid, malonic acid, oxalic acid, gluconic acid, camphorsulfonic acid, benzenesulfonic acid, acetic acid, propionic acid or p-toluenesulfonic acid.

The compounds of the formula I have asymmetric carbon atoms and can thus occur as enantiomers or diastereomers. The invention embraces both the pure isomers and the mixtures thereof. These mixtures of diastereomers can be fractionated into the components by conventional methods, for example selective crystallization from suitable solvents or chromatography on silica gel or aluminum oxide. Customary methods can be used to fractionate the racemates into the individual enantiomers, for example by salt formation with optically active acids, such as camphorsulfonic acid or dibenzoyltartaric acid, and selective crystallization, or by derivatization with suitable optically active reagents, separation of the diastereomeric derivatives and cleavage again.

The invention also relates to processes for the preparation of compounds of the formula I, which comprise (a) reaction, under conditions of the nucleophilic substitution, of a compound of the formula II

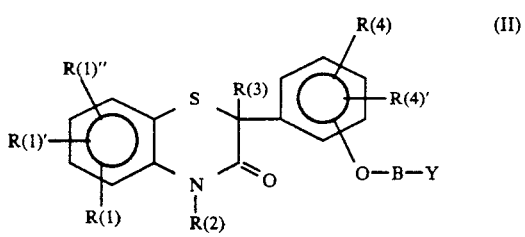

in which R(1), R(1)', R(1)'', R(2), R(3), R(4) and R(4)' have the same meaning as in formula I, and in which B denotes the radicals —$(CH_2)_m$—C≡C—$(CH_2)_n$ or —$(CH_2)_m$—CH=CH—$(CH_2)_n$, m and n having the same meaning as in formula I, and in which Y denotes a leaving group which can be displaced nucleophilically, in particular a chlorine, bromine or iodine atom, a radical of a sulfonic acid, preferably a methanesulfonyl radical, a benzenesulfonyl radical, a toluenesulfonyl radical or a trifluoromethanesulfonyl radical, with one of the compounds of the formulae IIIa, IIIb, IIIc, IIId or IIIe

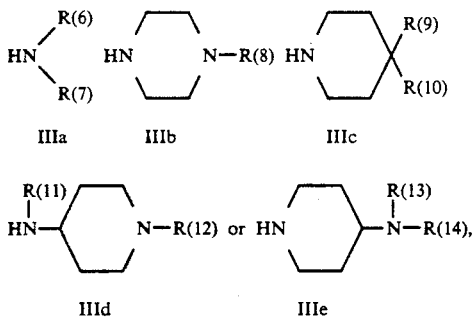

in which R(6), R(7), R(8), R(9), R(10), R(11), R(12), R(13) and R(14) have the same meaning as in formula I, preferably in a polar organic solvent such as an alcohol, preferably methanol, ethanol, propanol or isopropanol, or a lower ketone, preferably acetone or methyl ethyl ketone, or dimethylformamide, dimethyl sulfoxide or sulfolane, or a hydrocarbon, preferably toluene, with or without the presence of an auxiliary base to capture the acid which is formed by, preferably in the presence of potassium carbonate, sodium carbonate, triethylamine, N-ethylmorpholine or pyridine, at a temperature between 0° and 160° C., preferably between 20° and 120° C., or (b) reaction of a compound of the formula IV

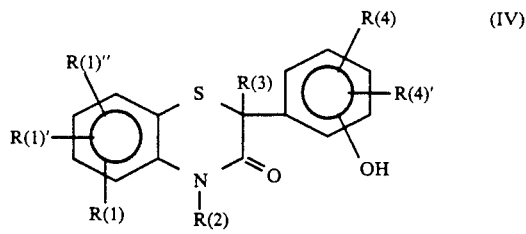

in which R(1), R(1)', R(1)'', R(2), R(3), R(4) and R(4)' have the same meaning as in formula I, with a compound of the formula V $$Z-(CH_2)_m-A-(CH_2)_n-R(5) \quad V$$

in which Z is defined in the same way as Y in formula II, and in which R(5) and A have the same meaning as in formula I, either in a polar aprotic solvent such as dimethylformamide, dimethyl sulfoxide, tetrahydrofuran, sulfolane or N-methylpyrrolidone, in the presence of a strong base such as sodium hydride, potassium hydride, sodium amide, lithium diisopropylamide, butyllithium or lithium hexamethyldisilazide, at a temperature between —40° and +60° C., preferably between —10° and —30° C., or in a protic or aprotic polar organic solvent such as a lower alcohol, for example methanol, ethanol or isopropanol, or a lower ketone, preferably acetone or methyl ethyl ketone, or in dimethylformamide, in the presence of a weak to moderately strong base, such as an alkali metal or alkaline earth metal hydroxide or carbonate, or an amine such as triethylamine, N-ethylmorpholine, N-methyldiisopropylamine or pyridine, at a temperature between 0° and 160° C., preferably between 20° and 120° C., or (c) reaction of a compound of the formula I in which A represents the group —C≡C—with an alkali metal, in particular lithium or sodium, in ammonia or an aliphatic amine, in particular an amine having 1 to 6 carbon atoms, at a temperature between —100° C. and the boiling point of the solvent, in particular at a temperature between —80° C. and —20° C., there being obtained a compound of the formula I in which A denotes a —CH=CH—group with the trans configuration, or (d) reaction, using a noble metal catalyst, in particular a catalyst of the type described by Lindlar (Helv. Chim. Acta 1952, 35, 446) or by Cram and Allinger (J. Am. Chem. Soc. 1956, 78, 2518), of a compound of the formula I in which A represents the group —C≡C—with hydrogen under a pressure of 1 to 20 bar in a hydrocarbon, an alcohol or an ester of a lower fatty acid, at a temperature between —20° C. and +60° C., there being obtained a compound of the formula I in which A denotes a double bond with the cis configuration.

Compounds of the formula II are obtained from compounds of the formula VIII $$Z-(CH_2)_m-A-(CH_2)_m-Y \quad VIII$$

in which A and Y have the same meaning as in formula II, and Z is a leaving group which can be displaced nucleophilically, Z being defined as Y and possibly being identical to or different from Y, under the conditions described under b).

Compounds of the formula IV are disclosed in EP-A 146,893.

Unless expressly mentioned otherwise, alkyl, alkylene, alkanoyl and alkoxy always mean straight or branched chains.

The compounds of the formula I, according to the invention, and their pharmacologically tolerated salts have calcium antagonistic or calcium agonistic properties depending on their structure. Hence they can be used for the treatment of all pathological states which derive from disturbance of the calcium balance in a warm-blooded animal. In particular, the compounds acting as calcium antagonists are suitable for the treatment of the cardiovascular system where there are appropriate symptoms, for example for various types of angina pectoris, tachycardia, cardiac dysrhythmias and high blood pressure. On the other hand, the compounds acting as calcium agonists can be used, for example, for the treatment of hypotension, of cardiac insufficiency of various etiologies, as well as of diabetes (type II).

The compounds according to the invention and their pharmacologically tolerated salts display their calcium antagonistic or calcium agonistic actions by influencing the influx of calcium ions into cells through specific channels.

Their action on the calcium channels can be shown using the biochemical test model of the displacement of tritium-labeled nitrendipine. In this test, membrane preparations which contain isolated calcium channels are loaded with the labeled substance. After incubation with the test substance, the radioactivity released and the radioactivity remaining on the membrane are determined. The $IC_{50}$ values shown by the compounds of the formula I, according to the invention, in this model are from $10^{-6}$ molar to $10^{-10}$ molar. For example, the compound from Example 2 has an $IC_{50}$ of $1.2 \times 10^{-10}$ M, and the compound from Example 3 has an $IC_{50}$ of $4.5 \times 10^{-10}$ M.

Their calcium antagonistic or calcium agonistic action can be shown using the model of the isolated rabbit aorta. This entails aorta rings being depolarized with potassium chloride, whereupon they contract. Pretreatment with the test substance is followed by a diminution in contraction in the case of the compounds acting as calcium antagonists, but by an intensification of contraction in the case of compounds acting as calcium agonists. For example, the compound from Example 2 at a concentration of $10^{-6}$ M results in a 32% diminution in contraction. The compound from Example 3 at a concentration of $10^{-6}$ M results in a 93% intensification of contraction.

The compounds according to the invention are active in a wide dose range. The level of the dose administered to warm-blooded species, especially to humans, depends on the nature of the desired treatment, on the mode of administration, on the condition, on the type and on the size of the treated mammal. On oral dosage, satisfactory results are attained with doses of from 0.01 mg, preferably from 0.1 mg, and up to 100 mg, preferably up to 20 mg, of a compound of the formula I per kg of body weight. In humans, the daily dose varies between 10 and 800 mg, preferably 20 to 500 mg, it being possible to give single doses of 5 to 200 mg, preferably once to three times a day.

The dose for intravenous and intramuscular administration is 1 to 300 mg, preferably 5 to 150 mg, a day.

The compounds of the present invention which can be used in pharmacology, and their salts, can be used for the preparation of pharmaceutical products which contain an effective amount of the active substance together with vehicles and which are suitable for enteral and parenteral administration. Use is preferably made of tablets or gelatin capsules which contain the active substance together with diluents, for example lactose, dextrose, sucrose, mannitol, sorbitol, cellulose and/or glycine, and lubricants such as diatomaceous earth, talc, stearic acid or its salts, such as magnesium or calcium stearate, and/or polyethylene glycol. Tablets additionally contain binders such as magnesium aluminum silicate, starch, gelatin, tragacanth, methylcellulose, sodium carboxymethylcellulose and/or polyvinylpyrrolidone and, if necessary, colorants, flavorings and sweeteners. Injectable products are preferably isotonic aqueous solutions or suspensions, which can be sterilized and contain auxiliaries such as preservatives, stabilizers, wetting agents and/or emulsifiers, solubilizers, salts to regulate the osmotic pressure, and/or buffer substances. The pharmaceutical products according to the invention, which, if desired, can contain further pharmacologically valuable substances, are prepared, for example, by conventional mixing, granulating and coating processes, and contain 0.1% to about 75%, preferably about 1% to about 50%, of the active substance.

The examples which now follow are intended to illustrate the invention without confining it to these examples.

EXAMPLE 1

(R)-2-[2-(4-chloro-2-butyn-1-yloxy)phenyl]-2-isopropyl-4-methyl-2H-1,4-benzothiazin-3(4H)-one 4.1 g (13 mmol) of R-2-(2-hydroxyphenyl)-2-isopropyl-4-methyl-2H-1,4-benzothiazin-3(4H)-one are dissolved in 10 ml of 1 N methanolic KOH, and the solution is heated to 50° C. A solution of 6.4 g (52 mmol) of 1,4-dichloro-2-butyne in 5 ml of methanol is added dropwise, with stirring, within 3 h. During this, a white precipitate separates out, and part of it settles on the wall. The reduction in the pH to below 6.5 is corrected during the subsequent reaction by several additions of 1 N methanolic KOH. The reaction is monitored by thin-layer chromatography (silica gel Si 60; mobile phase:cyclohexane/ethyl acetate 1:1) and is stopped after a total reaction time of about 6 h. The precipitate is filtered off with suction, washed with methanol and dried under high vacuum. 3.1 g (59%) of pure product (melting point 136° C.) are isolated in this way. The reaction yield can be increased to a total of 90% by working up the mother liquor.

EXAMPLE 2

(R)-2-Isopropyl-4-methyl-2-[2-[4-[4-(3,4,5-trimethoxyphenethyl)-1-piperazinyl]-2-butyn-1yloxy]phenyl]-2H-1,4-benzothiazin-3(4H)-one dihydrochloride 3.1 g (7.8 mmol) of the compound from Example 1 are mixed with 7 g (20 mmol) of 3,4,5-trimethoxyphenethylpiperazine and 10 g of potassium carbonate (finely ground), and 30 ml of isopropanol are added. The mixture is left to react at about 90° C. for 15 h, and is cooled, and then the salt is separated off. The dark brown filtrate is evaporated to a viscous oil (TLC check silica gel Si 60; mobile phase:dichloromethane/methanol 20:1).

The crude product is dissolved in acetone, and 5 ml of ethanolic HCl (2.5 N) are added. An impurity which separates out is removed, and the product is again evaporated and purified on a Lobar ®Si 60 column (mobile phase:dichloromethane/methanol 0:1). (Weight: 3.6 g 51%; melting point 166° C.; decomposition).

EXAMPLE 3

(R)-2-isopropyl-4-methyl-2-[2-[4-[4-(3,4,5-trimethoxy-phenethyl)-1-piperazinyl]-2-cis-buten-1-yloxy]phenyl]-2H-1,4-benzothiazin-3(4H)-one dihydrochloride 1.44 g (2 mmol) of the compound from Example 2 are dissolved in 10 ml of methanol and hydrogenated over a Lindlar catalyst, black (Fluka, 62 145), monitoring the hydrogen consumption. After the calculated amount of hydrogen has been absorbed, the catalyst is filtered off with suction, and the reaction product is examined by thin-layer chromatography (TLC on silica gel Si 60; mobile phase:a) n-butyl acetate/isopropanol/water/ammonia solution 30:50:15:5; b) chloroform/cyclohexane/ glacial acetic acid/ethanol 9:9:1:1).

The crude product is purified on a Lobar®Si 60 column using methylene chloride/methanol (20:1) as mobile phase (weight:420 29%; melting point 165° C., decomposition).

We claim:

1. A compound I of the formula

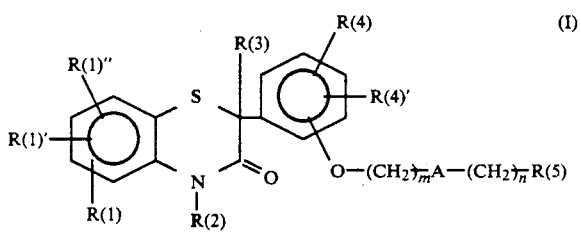

in which formula I:

R(1), R(1)' and R(1)" are identical or different and denote, independently of one another, hydrogen, $(C_1-C_4)$-alkyl, $(C_1-C_3)$-alkoxy, F, Cl, Br, $CF_3$, nitro, hydroxyl, acetamido or amino, R(2) denotes hydrogen, $(C_1-C_{10})$-alkyl, straight-chain or branched, $(C_3-C_{10})$-alkenyl, straight-chain or branched, phenyl-$(C_1-C_4)$-alkyl, the phenyl ring being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(3) denotes hydrogen, $(C_1-C_{15})$-alkyl, straight-chain or branched, $(C_3-C_{15})$-alkenyl, straight-chain or branched, $C_4-C_8$-cycloalkyl, $C_4-C_8$-cycloalkyl-$(C_1-C_4)$-alkyl, phenyl or phenyl-$(C_1-C_4)$-alkyl, each of the phenyl radicals being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy or nitro, R(4) and R(4)' are identical or different and denote, independently of one another, hydrogen, $(C_1-C_4)$alkyl, $(C_1-C_3)$-alkoxy, F, Cl, $CF_3$, nitro, hydroxyl, acetamido or amino, A denotes a group —C≡C— or a group —CH═CH— which has the cis or trans configuration, R(5) denotes one of the following groups

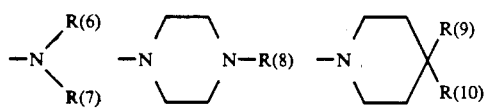

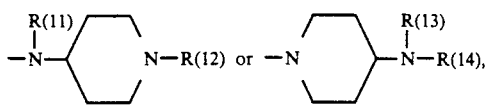

in which

R(6) and R(7) are identical or different and denote, independently of one another, hydrogen, $(C_1-C_{10})$alkyl, $C_4-C_8$)-cycloalkyl, $C_4-C_8$)-cycloalkyl-$(C_1-C_4)$-alkyl, pyridyl-$(C_1-C_4)$-alkyl, phenyl-$(C_1-C_6)$alkyl, benzhydryl or benzhydryl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(8) denotes hydrogen, $(C_1-C_{10})$-alkyl, straight-chain or branched, $C_1-C_8$-alkanoyl, pyridyl, pyrimidinyl, phenyl, phenyl-$(C_1-C_4)$-alkyl, phenyl-$(C_3-C_5)$alkenyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(9) denotes hydrogen, $(C_1-C_{10})$-alkyl, phenyl, phenyl-$(C_1-C_4)$-alkyl, each of the phenyl radicals be unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(10) denotes hydrogen, hydroxyl or $(C_1-C_4)$-alkoxy, and R(11) and R(12) or R(13) and R(14) are identical or different and denote, independently of one another, hydrogen, $(C_1-C_{10})$-alkyl, straight-chain or branched, $(C_1-C_6)$-alkanoyl, phenyl-$(C_1-C_4)$-alkyl, benzhydryl, or benzhydryl-$(C_1-C_4)$-alkyl, phenyl-$(C_1-C_4)$-alkanoyl or benzoyl, each of the phenyl radicals being unsubstituted or substituted by $(C_1-C_2)$-alkylenedioxy, F, Cl, Br, $CF_3$ or hydroxyl, m denotes 1, 2 or 3, and n denotes 1, 2 or 3, and the salts of the compounds of the formula I with pharmaceutically acceptable acids.

2. A compound I as claimed in claim 1, wherein at least one of the substituents or indices has the following meaning:

R(1) and R(1)', identical or different and independently of one another, hydrogen, methyl, ethyl, methoxy, ethoxy, fluorine, chlorine, $CF_3$, nitro or acetamido, R(1)" hydrogen, R(2) hydrogen, $(C_1-C_6)$-alkyl, straight-chain or branched, allyl, methallyl, benzyl, phenethyl, 4-methoxybenzyl, 3,4-dimethoxybenzyl, 3,4,5-trimethoxybenzyl, 3,4-methylenedioxybenzyl, R(3) hydrogen, $(C_1-C_{12})$-alkyl, straight-chain or branched, allyl, methallyl, $((C_5-C_7)$-cycloalkyl, $(C_5-C_7)$-cycloalkyl-$(C_1-C_4)$-alkyl, benzyl, methylbenzyl, fluorobenzyl, methoxybenzyl, dimethoxybenzyl or phenylethyl, R(4) hydrogen, methyl, methoxy, ethoxy, chlorine, nitro, hydroxyl, acetamido or amino, R(4)' hydrogen, A a group —C≡C— or a group —CH=CH— which has the cis or trans configuration, R(5) one of the following groups

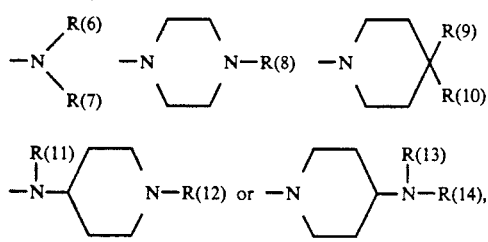

in which

R(6) denotes hydrogen, methyl, ethyl, propyl or isopropyl,

R(7) denotes hydrogen, methyl, ethyl, propyl, isopropyl, cyclopentylethyl, cyclohexylethyl, phenyl-$(C_1-C_4)$-alkyl, benzhydryl or benzhydryl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, $CF_3$ or hydroxyl, or denotes pyridyl-$(C_1-C_4)$-alkyl, R(8) denotes hydrogen, $(C_1-C_6)$-alkyl, straight-chain or branched, $(C_1-C_6)$-alkanoyl, phenyl, the phenyl radical being unsubstituted or substituted by one or two radicals from the group comprising $(C_1-C_4)$-alkyl, $(C_1-C_4)$-alkoxy, $(C_1-C_2)$-alkylenedioxy, F, Cl, $CF_3$ or hydroxyl, or denotes phenyl-$(C_1-C_4)$-alkyl, phenyl-$(C_3-C_5)$-alkenyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, ethyl, methoxy, ethoxy, $(C_1-C_2)$-alkylenedioxy, F, Cl, $CF_3$ or hydroxyl, R(9) denotes phenyl, phenyl-$(C_1-C_4)$-alkyl, each of the phenyl radicals being unsubstituted or substituted by one, two or three radicals from the group comprising $(C_1-C_4)$-alkyl, $(C_1-C_4)$-alkoxy, $(C_1-C_2)$-alkylenedioxy, F, Cl, $CF_3$ or hydroxyl, R(10) denotes hydrogen, hydroxyl or methoxy, R(11), R(12), R(13) and R(14) are identical or different and denote hydrogen, $C_1-C_8$-alkyl, $(C_1-C_6)$-alkanoyl, phenyl-$(C_1-C_4)$-alkyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, ethyl, methoxy, ethoxy, $(C_1-C_2)$-alkylenedioxy, F, Cl, $CF_3$ or hydroxyl, m 1 or 2, and n 1 or 2 and the salts of these compounds of the formula I with pharmaceutically acceptable acids.

3. A compound I as claimed in claim 1, wherein at least one of the substituents or of the indices has the following meaning:

R(1) hydrogen, methyl, methoxy, fluorine or chlorine,

R(1)' hydrogen or methoxy,

R(1)" hydrogen,

R(2) hydrogen, methyl, ethyl, propyl, isopropyl, butyl, sec. butyl, isobutyl, benzyl or phenethyl, R(3) hydrogen, $(C_1-C_{12})$-alkyl, straight-chain or branched, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) hydrogen, methoxy, methyl, chlorine, nitro or hydroxyl, R(4)' hydrogen, A a group —C≡C—, or a group —CH=CH— which has the cis or trans configuration, R(5) one of the following groups

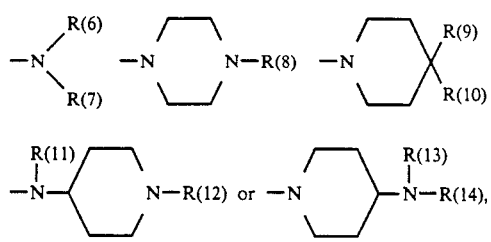

in which

R(6) denotes hydrogen or methyl,

R(7) denotes phenyl-$(C_1-C_4)$-alkyl, benzhydryl or benzhydryl-$(C_1-C_4)$-alkyl, each phenyl radical being unsubstituted or substituted by one, two or three radicals from the group comprising methyl, methoxy, fluorine, chlorine, methylenedioxy or hydroxyl, R(8) denotes $(C_1-C_6)$-alkyl, straight-chain or branched, $(C_1-C_6)$-alkanoyl, phenyl, phenyl-$(C_1-C_4)$-alkyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, methoxy, ethoxy, methylenedioxy, fluorine, chlorine or hydroxyl, R(9) denotes phenyl, the phenyl radical being unsubstituted or substituted by one, two or three radicals from the group comprising methyl, methoxy, fluorine, chlorine, methylenedioxy or hydroxyl, R(10) denotes hydrogen, hydroxyl or methoxy, R(11), R(12), R(13) and R(14) are identical or different and denote hydrogen, $(C_1-C_6)$-alkyl, $(C_1-C_6)$alkanoyl, phenyl-$(C_1-C_4)$-alkyl, benzhydryl or benzhydryl-$(C_1-C_4)$-alkyl, phenyl-$(C_1-C_4)$-alkanoyl or benzoyl, each of the phenyl radicals being unsubstituted or substituted by one, two or three radicals from the group comprising methyl, methoxy, methylenedioxy, fluorine, chlorine or hydroxyl, m and n 1, and the salts of these compounds of the formula I with pharmaceutically acceptable acids.

4. A pharmaceutical composition effective in the treatment of disorders of the cardiovascular system or disturbances of the blood glucose balance which comprises an effective amount of at least one compound as claimed in claim 1 in a pharmaceutically acceptable carrier.

5. A method for the treatment of disorders of the cardiovascular system which comprises administering an effective dose of a compound as claimed in claim 1.

6. A method for the treatment of disturbances of the blood glucose balance which comprises administering an effective dose of a compound as claimed in claim 1.

7. A method for the preparation of a medicament for the treatment of disorders of the cardiovascular system which comprises administering an effective dose of a compound as claimed in claim 1 in a pharmaceutically acceptable carrier.

8. A method for the preparation of a medicament for the treatment of disturbances of the blood glucose balance which comprises administering an effective dose of a compound as claimed in claim 1 in a pharmaceutically acceptable carrier.

* * * * *